(12) United States Patent
Choi et al.

(10) Patent No.: US 6,201,159 B1
(45) Date of Patent: Mar. 13, 2001

(54) PROCESS FOR THE CONTINUOUS PRODUCTION OF NEOPENTYL GLYCOL

(75) Inventors: Jung-Uk Choi; Seong-Moon Jung; Kee-Hyouk Lee; Ji-Joong Moon; Young-Jin Kim, all of Daejeon; Kwang-Ik Moon, Kyongju-shi, all of (KR)

(73) Assignee: LG Chemical Limited, Seoul (KR)

( * ) Notice: Subject to any disclaimer, the term of this patent is extended or adjusted under 35 U.S.C. 154(b) by 0 days.

(21) Appl. No.: 09/284,811

(22) PCT Filed: Oct. 22, 1997

(86) PCT No.: PCT/KR97/00199

§ 371 Date: Jun. 11, 1999

§ 102(e) Date: Jun. 11, 1999

(87) PCT Pub. No.: WO98/17614

PCT Pub. Date: Apr. 30, 1998

(30) Foreign Application Priority Data

Oct. 22, 1996 (KR) .................................................. 96-47517
Oct. 22, 1996 (KR) .................................................. 96-47518
Oct. 22, 1996 (KR) .................................................. 96-47519

(51) Int. Cl.[7] ..................................................... C07C 31/18

(52) U.S. Cl. ............................................. 568/853; 568/854

(58) Field of Search ...................................... 568/853, 854

(56) References Cited

U.S. PATENT DOCUMENTS

| 2,895,996 | * | 7/1959 | Wright | ................. | 568/853 |
| 3,920,760 | * | 11/1975 | Heinz | ................... | 568/853 |
| 3,939,216 | * | 2/1976 | Wright | ................. | 568/853 |
| 4,038,329 | * | 7/1977 | Palmer | ................. | 568/853 |
| 4,851,592 | * | 7/1989 | Morris | ................. | 568/853 |
| 4,855,515 | * | 8/1989 | Morris | ................. | 568/853 |
| 4,935,555 | * | 6/1990 | Elias | ................... | 568/853 |
| 5,532,417 | * | 7/1996 | Salek | ................... | 568/853 |

* cited by examiner

*Primary Examiner*—Michael L. Shippen
(74) *Attorney, Agent, or Firm*—Anderson Kill & Olick, PC

(57) ABSTRACT

A neopentyl glycol having a purity of 98% or more is produced continuously by a process comprising the steps of: conducting an aldol condensation of isobutyraldehyde with an aqueous formaldehyde solution containing methanol in an amount of 0.1 to 15 wt % in the presence of a tertiary alkylamine catalyst; extracting the condensation product mixture with octanol; distilling the extract; hydrogenating the distillation product; extracting the hydrogenation product mixture with water; and subjecting the extract to distillation.

14 Claims, 1 Drawing Sheet

PROCESS FOR THE CONTINUOUS PRODUCTION OF NEOPENTYL GLYCOL

FIELD OF THE INVENTION

The present invention relates to a process for the continuous production of high-purity neopentyl glycol.

BACKGROUND OF THE INVENTION

Neopentyl glycol (2,2-dimethyl-1,3-dihydroxypropane) is a white crystalline material widely used in the production of various industrial chemicals such as saturated and unsaturated polyesters, alkyl and polyurethane resins, powdered paints, synthetic lubricants, plasticizers, fiber processing agents and the like.

Neopentyl glycol is typically produced by an aldol condensation of isobutyraldehyde with formaldehyde, followed by hydrogenation over a metal catalyst, typically a nickel catalyst, as shown in the following Reaction Scheme:

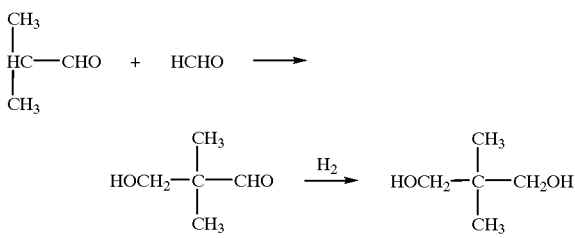

U.S. Pat. No. 3,808,280 discloses a process for producing neopentyl glycol by carrying out the aldol condensation reaction in the presence of a tertiary amine catalyst. This method has, however, the problem that the tertiary amine catalyst reacts with organic acids, generated via Cannizzaro reaction of aldehydes during the condensation process, to form salts. Such salts deactivate the metal catalyst used in the subsequent hydrogenation and decompose the aldol condensation product during the process of distillation at a high temperature, thus lowering the yield of the desired neopentyl glycol.

Accordingly, when an amine catalyst is employed in the condensation process, it is required to remove most of the organic acid by-products from the condensation products.

On the other hand, U.S. Pat. No. 4,885,515 discloses a process for hydrogenating the aldol condensation product under a high-temperature, high-pressure condition using a copper chromite catalyst containing manganese, instead of a conventional nickel catalyst. However, this method is hampered by the problems of catalyst deactivation and an increased equipment cost due to the requirement of a severe reaction condition.

The product mixture obtained after the aldol condensation may contain such by-products as isobutyl aldoxane and neopentyl glycol isobutyrate, in addition to the above-mentioned organic acids. When directly introduced to the hydrogenation step, said by-products convert to isobutanol and trimethylpentanediol (2,2,4-trimethyl-1,3-pentanediol), respectively, the latter having a boiling point similar to that of neopentyl glycol. This compound is thus difficult to separate from neopentyl glycol.

Accordingly, in order to obtain neopentyl glycol in a highly pure form, it is required to remove the above-mentioned by-products, as well as the remaining aldol condensation catalyst and unreacted reactants, prior to the hydrogenation step.

Crude neopentyl glycol obtained after the hydrogenation step typically contains trimethylpentanediol and neopentyl glycol monohydroxypivalate as by-products, which are difficult to separate from neopentyl glycol by simple distillation, due to similar boiling points thereof.

Many methods have been attempted to purify the crude neopentyl glycol, and these include solvent extraction, vacuum distillation and crystallization methods. U.S. Pat. No. 2,895,996 discloses a process for the purification of crude neopentyl glycol by conducting saponification, followed by sublimation, which exploits the fact that neopentyl glycol is easily sublimable. However, this method is not commercializable due to the requirement that a low temperature must be maintained at the top of the sublimation apparatus.

Further, U.S. Pat. No. 4,935,555 suggests a method of distilling crude neopentyl glycol by using a membrane distillation apparatus under vacuum. However, this method requires expensive equipments, and gives a low yield of neopentyl glycol.

SUMMARY OF THE INVENTION

It is, therefore, an object of the present invention to provide an economical, commercializable process for continuously producing highly pure neopentyl glycol.

In accordance with an aspect of the present invention, there is provided a process for the production of neopentyl glycol which comprises:

(a) reacting isobutyraldehyde with an aqueous formaldehyde solution containing methanol in an amount ranging from 0.1 to 15 wt % in the presence of a tertiary alkylamine catalyst to obtain an aldol condensation product mixture containing hydroxypivaldehyde;

(b) extracting the condensation product mixture with an organic solvent to produce a first organic phase mixture containing hydroxypivaldehyde and a first aqueous phase mixture;

(c) distilling the first organic phase mixture obtained in step (b) to obtain a low-boiling compound mixture containing materials having boiling points lower than that of hydroxypivaldehyde, and a second organic phase mixture;

(d) hydrogenating the second organic phase mixture obtained in step (c) in the presence of a nickel catalyst to obtain a hydrogenation product mixture containing neopentyl glycol;

(e) extracting the hydrogenation product mixture with water to obtain a second aqueous phase mixture containing neopentyl glycol and a third organic phase mixture;

(f) subjecting the second aqueous phase mixture obtained in step (e) to an azeotropic distillation to obtain a distillation product which is a mixture of neopentyl glycol and water as well as a distillation bottom product; and (g) distilling the mixture of neopentyl glycol and water obtained in step (f) to obtain neopentyl glycol.

BRIEF DESCRIPTION OF DRAWING

The above and other objects and features of the present invention will become apparent from the following description, taken in conjunction with the accompanying drawing, wherein.

DETAILED DESCRIPTION OF THE INVENTION

A. Condensation

Figure 1:
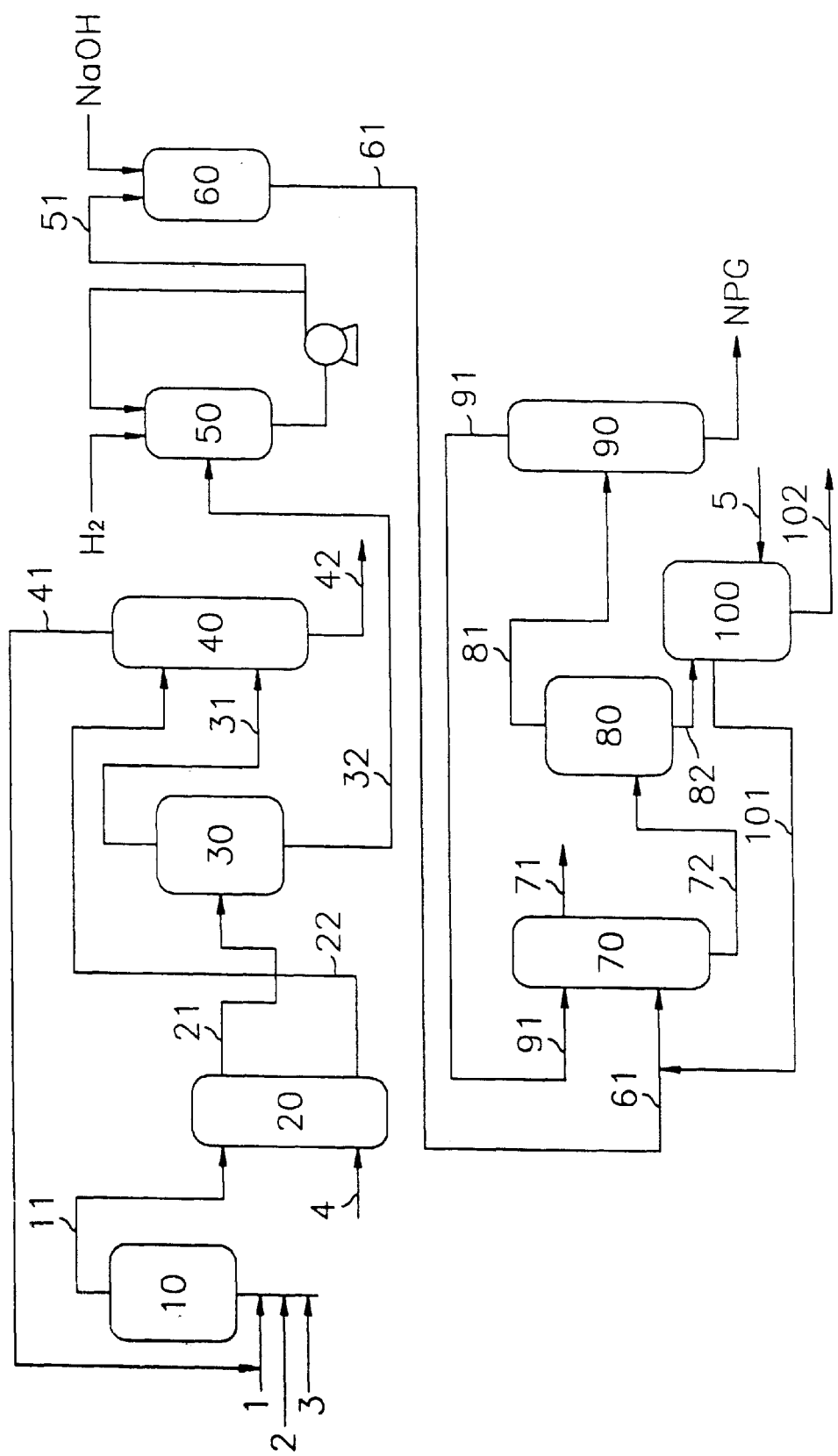
FIG. 1 is a schematic flow diagram showing a process for the continuous production of pure neopentyl glycol in accordance with a preferred embodiment of the present invention.

As the first step of the inventive process for the production of neopentyl glycol, isobutyraldehyde is reacted with an aqueous formaldehyde solution in the presence of a tertiary alkylamine catalyst to provide an aldol condensation product mixture containing hydroxypivaldehyde.

The aqueous formaldehyde solution employed in the aldol condensation of the present invention comprises methanol in an amount of 0.1 to 15%, preferably 0.1 to 5% by weight. Further, isobutyraldehyde may be employed in an amount ranging from 1.0 to 1.3 moles per 1 mole of formaldehyde employed. The tertiary alkylamine employed as a catalyst may be preferably trialkylamine and may be employed in an amount ranging from 0.03 to 0.06 mole per 1 mole of formaldehyde employed.

The condensation process may be preferably conducted at a temperature ranging from 70 to 90° C. and for a period ranging from 1 to 3 hours.

B. Purification of Hydroxypivaldehyde by Extraction and Distillation

The condensation product mixture is then subjected to an extraction step to recover hydroxypivaldehyde therefrom. The extraction may be conducted counter-currently by adding a water-immiscible organic solvent to the condensation product mixture at a temperature ranging from 40 to 70° C. In this counter-current extraction step, hydroxypivaldehyde is transferred from the aqueous condensation product phase to the organic phase.

The water-immiscible organic solvent which may be employed in the present invention include $C_{6-18}$ organic solvents, preferably aliphatic alcohols, most preferably octanol; and it may be employed in an amount ranging from 0.3 to 4 times the weight of hydroxypivaldehyde employed.

In addition to the water-immiscible organic solvent, water may be employed in an amount of 1 to 2 times the weight of hydroxypivaldehyde introduced to the extraction step, for the purpose of effective removal of water soluble by-products present in the condensation product mixture, e.g., organic acids and triethylamine salts thereof.

Subsequently, the organic phase extract containing hydroxypivaldehyde is distilled to separate materials having boiling points lower than that of hydroxypivaldehyde, e.g., isobutyraldehyde, triethylamine and water. The distillation bottom entrained hydroxypivaldehyde at a recovery rate of 99% or more.

The mixture of low-boiling materials obtained above may be sent to an extractive distillation step in order to recover triethylamine and isobutyraldehyde. In this extractive distillation step, the aqueous phase containing the condensation by-products obtained in the extraction step is combined with the mixture of low-boiling materials recovered in the distillation step, and the materials recovered in the extractive-distillation step may be recycled to the condensation step.

C. Hydrogenation

Hydroxypivaldehyde obtained as described previously is subsequently hydrogenated in the presence of a nickel catalyst to produce crude neopentyl glycol. The nickel catalyst may be a Raney nickel catalyst composed of Ni 85–90 wt %, Al 8–12 wt %, Mo 1–4 wt % and Fe 0.1–0.8 wt %; and the catalyst may be employed in an amount ranging from 2 to 10% by weight based on the weight of hydroxypivaldehyde introduced. The temperature and pressure employed in the hydrogenation step may range from 120 to 180° C., preferably 140 to 160° C., and from 100 to 1,500 psig, preferably 700 to 1,000, respectively.

In order to enhance the gas-liquid contact in the hydrogenation process, a part of the hydrogenation product mixture may be recycled to the hydrogenation step. The reactor which may be employed for this purpose is a loop-type reactor having a nozzle located at the top, which enables recycling of a part of the product at a high speed.

If desired, the hydrogenation product mixture containing the crude neopentyl glycol may be subjected to a saponification step prior to the neopentyl glycol extraction step described below. In the saponification step, neopentyl glycol precursors such as neopentyl glycol monohydroxy-pivalate present in the hydrogenation product mixture may be converted to neopentyl glycol. The saponification step is conducted by a conventional method using an alkali such as sodium hydroxide.

D. Purification of Neopentyl Glycol by Extraction and Distillation

The hydrogenation product mixture containing neopentyl glycol is subsequently extracted with water. In this extraction step, the hydrogenation product mixture and water are contacted countercurrently, wherein water may be employed in an amount ranging from 0.5 to 4 times, preferably 1 to 1.5 times the weight of neopentyl glycol. The extraction may be conducted at a temperature ranging from 10 to 50° C. In accordance with the present invention, neopentyl glycol is transferred to an aqueous phase, but by-products remain in the organic phase. Therefore, in accordance with the present invention, neopentyl glycol can be easily isolated from by-products at an ambient temperature.

The extract obtained in this extraction step, an aqueous phase mixture, comprises neopentyl glycol and water in a weight ratio of about 4:6 to about 9:1.

Thereafter, the aqueous phase mixture containing neopentyl glycol is subjected to an azeotropic distillation process. In this step, a mixture of neopentyl glycol and water is distilled to separate and remove small amount of impurities, e.g., salts of organic acids. In order to increase the efficiency, the azeotropic distillation process may be conducted using a column packaged with materials which are capable of trapping said impurities.

The mixture of neopentyl glycol and water thus evaporated is then directly introduced in the form of a vapor to a distillation step wherein it is distilled to separate water and obtain pure neopentyl glycol. Water thus separated may be recycled to the water extraction step.

Alternatively, the azeotropic distillation and the final distillation steps may be integrated into one step. In this case, the mixture of neopentyl glycol and water may be preferably sparged to the bottom of an integrated distillation column.

On the other hand, the azeotropic distillation residue containing organic acid impurities may also contain some residual neopentyl glycol and this fraction may be extracted with an organic solvent, preferably octanol, in a countercurrent mode, for the purpose of recovering neopentyl glycol remaining therein. This extraction procedure may be preferably conducted using a multi-stage extraction apparatus in a continuous manner. The organic phase extract containing neopentyl glycol may then be recycled to the water extraction step.

In accordance with the present invention, the rate of recovery of neopentyl glycol produced in the hydrogenation step may reach 98% or more. The pure neopentyl glycol product thus obtained may be formed into flakes using a conventional flaker or may be mixed with water under a pressure of 0.1 to 5 kg/cm² to form an aqueous solution.

PREFERRED EMBODIMENT OF THE INVENTION

In accordance with a preferred embodiment of the present invention, pure neopentyl glycol may be continuously produced as follows:

Specifically, referring to a schematic flow diagram shown in FIG. 1, an aqueous solution of formaldehyde is continuously fed via pipe (2), and isobutyraldehyde and a tertiary amine such as triethylamine are continuously fed via pipes (1) and (3), respectively, to aldol condensation reactor (10) where an aldol condensation product mixture containing crude hydroxypivaldehyde is obtained.

The condensation product mixture is then led from the top of reactor (10) to the upper region of extractor (20) via pipe (11) while octanol is introduced separately via pipe (4) to the lower region of extractor (20) wherein hydroxypivaldehyde is transferred from the condensation product mixture to the organic phase. At this time, water may be added to extractor (20) together with octanol in order to enhance the removal of water-soluble impurities, if necessary.

The organic phase containing crude hydroxypivaldehyde is transferred from the upper region of extractor (20) via pipe (21) to distillation column (30) wherein low boiling materials, such as excess isobutyraldehyde, triethylamine and water, are removed.

The organic phase containing purified hydroxypivaldehyde is then continuously drawn from the bottom of column (30) and fed via pipe (32) to hydrogenation reactor (50), while the mixture of low boiling materials leaving the top of column (30) is introduced via pipe (31) to extractive distillation column (40) to be treated together with the aqueous phase mixture introduced from the bottom of column (20) via pipe (22).

In extractive distillation column (40), low boiling materials are recovered and recycled via pipe (41) to reactor (10) for reuse, and the remaining solution is discarded via pipe (42).

In hydrogenation reactor (50), the organic phase mixture containing purified hydroxypivaldehyde contacts with hydrogen gas fed separately in the presence of a Raney nickel catalyst to produce a hydrogenation product mixture containing crude neopentyl glycol. At this time, a part of the hydrogenation product mixture may be recycled to hydrogenation reactor (50), using a nozzle positioned at the top and a high-speed pump, in order to enhance the liquid-gas contact.

The hydrogenation product mixture is then transferred via pipe (51) to saponificator (60) wherein it mixes with sodium hydroxide fed separately, and neopentyl glycol esters of, e.g., hydroxypivalic acid undergo hydrolysis to recover neopentyl glycol.

The output from saponificator (60) is then introduced via pipe (61) to the bottom region of extractor (70) wherein it meets countercuzrently with water, freshly introduced or recycled from distillation column (90) to the upper region of extractor (70), wherein neopentyl glycol is transferred from the organic phase to the aqueous phase.

The organic phase is released via pipe (71) while the aqueous phase is drained out from the bottom of extractor (70) and then sparged continuously to the lower region of azeotropic distillation column (80) via pipe (72), wherein a mixture of neopentyl glycol and water is separated from organic salt impurities. A part of the upper region of column (80) is packaged with materials capable of preventing the passage of the organic salt impurities.

The vapor mixture of neopentyl glycol and water is continuously transferred from the top of column (80) to distillation column (90) via pipe (81). Water condensed at the top of column (90) is recycled to extractor (70) via pipe (91), while the desired pure neopentyl glycol is recovered as a bottom product of distillation column (90).

The azeotropic distillation residue containing organic salt impurities as well as some residual amount of neopentyl glycol is taken out from the bottom of column (80) and introduced via pipe (82) to the upper region of extractor (100), where it contacts countercurrently an organic solvent which is separately fed to the lower region of extractor (100) via pipe (5). The organic phase containing recovered neopentyl glycol is drawn from the upper region of extractor (100) and then recycled to the lower region of extractor (70) via pipe (101). The aqueous phase drained from the bottom of extractor (100) is discarded via pipe (102).

As described previously, in accordance with the present invention, neopentyl glycol may be produced in a high purity by way of purifying crude hydroxypivaldehyde or neopentylglycol by a series of an extraction, distillation and extractive distillation process.

The following examples are only provided for the purposes of illustrating certain aspects of the present invention; they are not to be construed as limiting the scope of the present invention in any way.

EXAMPLE 1

Production of hydroxypivaldehyde

A 20 liter reactor equipped with a stirrer was continuously fed with isobutyraldehyde, 38% formaldehyde aqueous solution (methanol content 0.3% ) and triethylamine at rates of 46.8 g/min, 42.2 g/min, and 2.6 g/min, respectively. The reactor was maintained at 70 to 90° C. under a nitrogen pressure of 10 to 40 psi.

The residence time was adjusted at 1 hour and the condensation product mixture containing crude hydroxypivaldehyde was removed from the reactor at a rate of 91.6 g/min.

This condensation product mixture having the composition shown in Table 1 was introduced continuously to the upper region of a multi-stage extractor, where the condensation product stream contacts an octanol stream fed separately to the lower region of the extractor. This countercurrent extraction of the condensation product mixture with octanol removes most of trimethylamine salts of organic acids and unreacted reactants from the condensation product stream containing hydroxypivaldehyde.

The multi-stage extractor having a diameter of 60 mm and 30 stages was equipped with a stirrer and a water jacket for maintaining a constant temperature of 30 to 70° C. The rate of stirring in the extractor was 80 rpm. No significant loss of hydroxypivaldehyde was observed in this extraction step, and the composition of the crude hydroxypivaldehyde stream exiting the extractor is shown in Table 1.

The crude hydroxypivaldehyde stream from the extractor was then introduced to a glass distillation column having a diameter of 50 mm and 15 stages (constructed by Oldshaw, Shott, Germany) and distilled to recover low boiling point materials such as isobutyraldehyde and triethylamine at a column bottom temperature of 80 to 110° C. under a pressure of 400 to 700 mbar.

An aqueous distillate containing the low boiling point materials recovered from the top of the distillation column was recycled to the aldol condensation reactor, while a mixture containing hydroxypivaldehyde having the composition shown in Table 1 was recovered from the bottom of the column.

TABLE 1

|  | After condensation step (wt %) | After extraction step (wt %) | After distillation step (wt %) |
|---|---|---|---|
| Methanol | 0.5 | 0.25 | — |
| Isobutanol | — | — | — |
| Water | 28.9 | 10.8 | 5.88 |
| Octanol | — | 26.69 | 30.68 |
| Isobutyraldehyde | 7.4 | 6.69 | 0.98 |
| Triethylamine and organic salts | 4.6 | 2.41 | 0.54 |
| Hydroxypivaldehyde | 52.6 | 47.81 | 56.33 |
| Neopentylglycol | 1.2 | 1.08 | 0.92 |
| Neopentylglycol ester | 3.0 | 2.73 | 4.22 |
| Others | 1.8 | 1.54 | 0.45 |

EXAMPLE 2

Production of crude neopentyl glycol

A product mixture containing hydroxypivaldehyde obtained as in Example 1 was continuously introduced at a rate of 13 g/min to a 2 liter autoclave equipped with a stirrer and the hydrogenation was carried out to produce a mixture containing crude neopentyl glycol. The hydrogenation was conducted at 150° C. under a hydrogen pressure of 1,000 psi for 26 hours in the presence of a Raney nickel catalyst in an amount of 6% by weight based on the weight of hydroxypivaldehyde employed. No significant catalyst deactivation was observed during a 80 hour run.

The changes in the composition before and after the hydrogenation step are shown in Table 2.

TABLE 2

|  | Before Hydrogenation step (wt %) | After hydrogenation step (wt %) |
|---|---|---|
| Methanol | 0.25 | 0.37 |
| Isobutanol | 0.06 | 2.02 |
| Water | 6.31 | 6.23 |
| Octanol | 35.17 | 34.72 |
| Isobutyraldehyde | 2.29 | 0.35 |
| Triethylamine | 1.11 | 1.10 |
| Hydroxypivaldehyde | 48.45 | — |
| Neopentylglycol | 3.95 | 52.96 |
| Neopentylglycol ester | 1.54 | 1.52 |
| Trimethylpentanediol | 0.74 | 0.73 |
| Others | 0.13 | — |

EXAMPLE 3

Extraction of neopentyl glycol

A hydrogenation product mixture containing crude neopentyl glycol obtained as in Example 2 was continuously introduced to the lower region of an extractor at a flow rate of 215 g/min while water was continuously introduced to the upper region of the extractor at a flow rate of 175 g/min. In this counter-current extraction step, neopentyl glycol in the hydrogenation product mixture was transferred to the aqueous phase.

The extractor was made of glass and had an inner diameter of 60 mm, height of 3 m and 50 stages. The extractor was a Scheibel type equipped with a stirrer on the upper region for enhancing countercurrent contact of the hydrogenation product mixture with water. The extraction process was conducted at 30° C. and a contact time of 25 minutes.

The aqueous phase containing neopentyl glycol was drained out from the bottom of the extractor at a flow rate of 293.8 g/min and the organic phase was fluxed from the top of extractor at a flow rate of 93.04 g/min. The efficiency of the extraction was 99.2%.

The compositions of the hydrogenation product mixture introduced and the aqueous and organic streams obtained from the extraction process are shown in Table 3.

TABLE 3

|  | Hydrogenation product mixture (wt %) | Organic phase after extraction (wt %) | Aqueous phase after extraction (wt %) |
|---|---|---|---|
| Neopentylglycol | 48.8 | 1.17 | 31.88 |
| Octanol | 40.9 | 86.98 | 3.63 |
| water | 6.78 | 9.03 | 63.19 |
| Materials having low boiling temp. | — | — | — |
| TMPD | 0.42 | 0.42 | 0.1 |
| HPNE | 3.1 | 2.4 | 1.2 |

*TMPD: Trimethylpentane diol
*HPNE: Neopentyl glycol ester of hydroxypivalic acid

EXAMPLE 4

A hydrogenation product mixture obtained as in Example 2 was saponificated by the addition of NaOH, prior to the extraction step according to Example 3, for the purpose of converting neopentyl glycol monohydroxypivalate present in the hydrogenation product mixture to neopentyl glycol and sodium hydroxypivalate. Subsequently, the extraction process was conducted at 32° C. and a contact time of 30 minutes.

The aqueous phase containing neopentyl glycol was recovered from the bottom of the extractor at a flow rate of 298.8 g/min and the organic phase was vent off from the top of column at a flow rate of 88.9 g/min. The efficiency of the extraction was 99.43%.

The analytical results of the saponification and extraction experiment are shown in Table 4.

TABLE 4

|  | Hydrogenation product mixture (wt %) | Organic phase after extraction (wt %) | Aqueous phase after extraction (wt %) |
|---|---|---|---|
| Neopentylglycol | 47.7 | 0.38 | 30.71 |
| Octanol | 38.7 | 89.92 | 2.35 |
| water | 10.8 | 8.9 | 66.04 |
| Materials having | — | — | — |

TABLE 4-continued

|  | Hydrogenation product mixture (wt %) | Organic phase after extraction (wt %) | Aqueous phase after extraction (wt %) |
|---|---|---|---|
| low boiling temp. |  |  |  |
| TMPD | 0.4 | 0.6 | 0.1 |
| HPNE | 0.1 | 0.2 | — |
| Sodium salt | 2.3 | — | 0.8 |

As shown in Table 4, the levels of TMPD and HPNE in the aqueous extract are greatly reduced by the inclusion of a saponification step.

EXAMPLE 5

Purification of neopentyl glycol

An aqueous phase obtained after the extraction process as in Example 4 was continuously introduced at a flow rate of 20 g/min to the bottom of an azeotropic distillation column using a sparger.

The azeotropic distillation column was a 1 m long glass column having a diameter of 30 mm and it was packaged with glass raschig ring in the height of 30 cm from the top. The top region of the column was maintained at 118 to 123° C. and the bottom region was maintained at 130 to 135° C. The azeotropic distillation was conducted under a pressure of 320 to 330 mbar.

(1) Recovery and recycling residual neopentyl glycol present in the azeotropic distillation bottom The bottom product stream from the azeotropic distillation column was mixed with water in a weight ratio of 1:0.6 and the resulting mixture was continuously introduced to the upper region of a multi-stage extractor at a flow rate of 29.8 g/min. Separately, octanol was introduced to the lower region of the extractor at a flow rate of 37.4 g/min. In this counter-current extraction conducted at 75° C., neopentyl glycol was transferred to the octanol stream.

The octanol stream containing neopentyl glycol was fluxed from the top of the extractor at a flow rate of 51.4 g/min and then recycled to the extractor of Example 4. Further, the aqueous phase containing water soluble salts was drained out from the bottom of the extractor at a flow rate of 13.1 g/min and then discarded.

The rate of recovery of neopentyl glycol originally present in the bottom product was 98.6% and 95.9% of the sodium salts was removed.

The compositions of the bottom product of the azeotropic distillation column, and the products obtained at the top and the bottom of the extractor were analyzed by gas chromatography and the results are shown in Table 5.

TABLE 5

|  | Bottom product of azeotropic distillation column (wt %) | Top product of the extractor (wt %) | Bottom product of the extractor (wt %) |
|---|---|---|---|
| Neopentylglycol | 43.67 | 23.72 | 1.37 |
| Water | 37.61 | 6.10 | 60.38 |
| Sodium salts | 18.72 | 1.11 | 38.02 |
| Octanol | — | 69.08 | 0.23 |

(2) Final purification of neopentyl glycol

The product stream leaving the top of the azeotropic distillation column, on the other hand, was continuously introduced to a position between the 8th stage and the 12th stage of a multi-stage distillation column having 15 stages. The temperature at the top region of this distillation column was 66 to 68° C. and the temperature at the bottom region was 175 to 180° C. The aqueous solution was condensed at the top region and then removed at a flow rate of 6 to 6.5 g/min while a highly pure neopentyl glycol stream was recovered at a flow rate of 13.5 to 14.0 g/min at the bottom of the column.

The compositions of the aqueous phase product obtained after the extraction, and the products obtained at the top and the bottom of the distillation column were analyzed by gas chromatography and the results are shown in Table 6.

TABLE 6

|  | Aqueous phase product obtained after extraction (wt %) | Top product of the distillation column (wt %) | Bottom product of the distillation column (wt %) |
|---|---|---|---|
| Neopentylglycol | 30.81 | — | 99.5 |
| Water | 67.6 | 99.35 | 0.15 |
| Sodium salts | 1.0 | — | — |
| Octanol | 0.4 | 0.5 | 0.05 |
| TMPD | 0.09 | — | 0.25 |
| Others | 0.1 | 0.15 | 0.05 |

As clearly seen from the results of Examples 1 to 5, in accordance with the present invention, highly pure neopentyl glycol can be continuously and economically produced.

While the invention has been described with respect to the specific embodiments, it should be recognized that various modifications and changes may be made by those skilled in the art to the invention which also fall within the scope of the invention as defined by the appended claims.

What is claimed is:

1. A process for the production of neopentyl glycol which comprises the steps of:
   (a) reacting isobutyraldehyde with an aqueous formaldehyde solution containing methanol in an amount ranging from 0.1 to 15 wt % in the presence of a tertiary alkylamine catalyst to obtain an aldol condensation product mixture containing hydroxypivaldehyde;
   (b) extracting the condensation product mixture with an organic solvent to produce a first organic phase mixture containing hydroxypivaldehyde and a first aqueous phase mixture;
   (c) distilling the first organic phase mixture obtained in step (b) to obtain a low-boiling compound mixture containing materials having boiling points lower than that of hydroxypivaldehyde, and a second organic phase mixture;

(d) hydrogenating the second organic phase mixture obtained in step (c) in the presence of a nickel catalyst to obtain a hydrogenation product mixture containing neopentyl glycol;

(e) extracting the hydrogenation product mixture with water to obtain a second aqueous phase mixture containing neopentyl glycol, and a third organic phase mixture;

(f) subjecting the second aqueous phase mixture obtained in step (e) to an azeotropic distillation to obtain a distillation product which is a mixture of neopentyl glycol and water as well as a distillation bottom product; and (g) distilling the mixture of neopentyl glycol and water obtained in step (f) to obtain neopentyl glycol.

2. The process of claim 1 further comprising the steps of combining the first aqueous phase mixture obtained in step (b) and the low-boiling compound mixture obtained in step (c), subjecting the combined mixture to an extractive distillation and recycling the extract to the condensation step (a).

3. The process of claim 1 wherein the aqueous formaldehyde solution comprises methanol in an amount of 0.1 to 5 wt %.

4. The process of claim I wherein the organic solvent employed in step (b) is octanol.

5. The process of claim 3 wherein the organic solvent is employed in an amount ranging from 0.3 to 4 times the weight of the hydroxypivaldehyde introduced.

6. The process of claim 4 wherein water is further employed in an amount of 1 to 2 times the weight of hydroxypivaldehyde introduced, together with octanol.

7. The process of claim 1 wherein the hydrogenation step (d) is conducted at a temperature ranging from 120 to 180° C. and a pressure ranging from 100 to 1,500 psig.

8. The process of claim 1 wherein a part of the hydrogenation product mixture is recycled to the hydrogenation step (d) using a loop-type reactor.

9. The process of claim 1 further comprising the step of saponificating the product mixture obtained in the hydrogenation step (d) using an alkali.

10. The process of claim 1 wherein the amount of water employed in the extraction step (e) is 0.5 to 4 times the weight of neopentyl glycol introduced.

11. The process of claim 1 wherein the extraction step (e) is conducted at a temperature ranging from 10 to 50° C.

12. The process of claim 1 wherein the second aqueous phase mixture obtained in step (e) contains 10 to 60% by weight of water.

13. The process of claim 1 further comprising the step of extracting the distillation bottom product obtained in the azeotropic distillation step (f) with an organic solvent to recover neopentyl glycol therefrom.

14. The process of claim 1 wherein the distillation product obtained by the azeotropic distillation step (f) is introduced in the form of a vapor to the distillation step (g).

* * * * *